United States Patent
Olek

(10) Patent No.: US 11,976,327 B2
(45) Date of Patent: May 7, 2024

(54) ERGIC1 AS EPIGENETIC MARKER FOR THE IDENTIFICATION OF IMMUNE CELLS, IN PARTICULAR MONOCYTIC MYELOID-DERIVED SUPPRESSOR CELLS (MMDSCS)

(71) Applicant: Precision for Medicine GmbH, Berlin (DE)

(72) Inventor: Sven Olek, Berlin (DE)

(73) Assignee: Precision for Medicine GmbH, Berlin (DE)

( * ) Notice: Subject to any disclaimer, the term of this patent is extended or adjusted under 35 U.S.C. 154(b) by 88 days.

(21) Appl. No.: 16/762,534

(22) PCT Filed: Nov. 6, 2018

(86) PCT No.: PCT/EP2018/080235
§ 371 (c)(1),
(2) Date: May 8, 2020

(87) PCT Pub. No.: WO2019/091942
PCT Pub. Date: May 16, 2019

(65) Prior Publication Data
US 2020/0347453 A1    Nov. 5, 2020

(30) Foreign Application Priority Data
Nov. 9, 2017   (DE) .......................... 102017126248.2

(51) Int. Cl.
*C12Q 1/6883*   (2018.01)
(52) U.S. Cl.
CPC ..... *C12Q 1/6883* (2013.01); *C12Q 2600/154* (2013.01)
(58) Field of Classification Search
None
See application file for complete search history.

(56) References Cited

U.S. PATENT DOCUMENTS

2016/0237493 A1   8/2016   Brandon et al.

FOREIGN PATENT DOCUMENTS

| WO | 2012162660 A2 | 11/2012 |
| WO | 2014170497 A2 | 10/2014 |
| WO | 2015159292 A2 | 10/2015 |

OTHER PUBLICATIONS

Ehrlich et al. Oncogene 2002. 21: 5400-5413 (Year: 2002).*
Adalsteinsson et al PLoS One. Oct. 2012 . . . 7(10): e0046705 (Year: 2012).*
Hegde et al (Immunity. May 11, 2021. 54(5): 875-884 (Year: 2021).*
Cassetta (Cancer Immunology, Immunotherapy. 2019. 68: 687-697 (Year: 2019).*
Booth et al., Quantitative Sequencing of 5-Methylcytosine and 5-Hydroxymethylcytosine at Single-Base Resolution Science, May 18, 2012, vol. 336, No. 6083, pp. 934-937.
Esteller, CpG Island Hypermethylation and Tumor Suppressor Genes: a Booming Present, a Brighter Future, Oncogene 21:5427-5440, 2002.
Jones and Lair, Cancer Epigenetics Comes of Age, Nature Genetics, vol. 1, pp. 163-167, Feb. 1999.
Kallinteris et al., Results of epigenetic-based quantitative PCR assisted immune cell counting analysis in bavituximab SUNDRISE trial subgroup, Journal for Immunotherapy of Cancer, Biomed Central Ltd. NLD, vol. 5, Supplemental 2:86, Nov. 1, 2017.
Kirby et al., Genome-wide DNA methylation measurements in prostate tissues uncovers novel prostate cancer diagnostic biomarkers and transcription factor binding patterns, BMC Cancer 2017 (1); 273, pp. 1-10.
Kristensen and Hansen, PCR-Based Methods for Detecting Single-Locus DNA Methylation Biomarkers in Cancer Diagnostics, Prognostics, and Response to Treatment, Clinical Chemistry 55:8 1471-1483 (2009).
Laird, P.W., The Power and the Promise of DNA Methylation Markers, Nature Reviews/Cancer 3:253-266, Apr. 2003.
Zhang et al., Epigenetics in myeloid derived suppressor cells: a sheathed sword towards cancer, Oncotarget (Aug. 30, 2016) 7 (35): 57452-57463.

* cited by examiner

*Primary Examiner* — Carla J Myers
(74) *Attorney, Agent, or Firm* — BakerHostetler

(57) ABSTRACT

The present invention relates to a method, in particular an in vitro method, for identifying specific immune cells, in particular MDSCs, comprising analyzing a modification, preferably the methylation status, of at least one CpG position in the mammalian gene region for endoplasmatic reticulum-golgi intermediate compartment 1 (ERGIC1), wherein a demethylation or lack of methylation or modification of said gene region is indicative for an MDSC, when compared to a non-MDSC. The analyses according to the invention can identify specific sub-populations of MDSCs, namely monocytic MDSCs (m MDSCs) on an epigenetic level and distinguish them from all other cells in complex samples, such as, for example, other blood or immune cells. The present invention furthermore provides an improved method for quantifying m MDSCs, in particular in complex samples. The method can be performed without a step of purifying and/or enriching cells, preferably in whole blood and/or non-trypsinized tissue.

16 Claims, 2 Drawing Sheets
Specification includes a Sequence Listing.

ERGIC1 AS EPIGENETIC MARKER FOR THE IDENTIFICATION OF IMMUNE CELLS, IN PARTICULAR MONOCYTIC MYELOID-DERIVED SUPPRESSOR CELLS (MMDSCS)

CROSS-REFERENCE TO RELATED APPLICATIONS

This application is a 35 U.S.C. § 371 national phase application of International Patent Application No. PCT/EP2018/080235, filed Nov. 6, 2018, which claims priority to German Patent Application No. 102017126248.2, filed Nov. 9, 2017, the entire disclosures of each of which are incorporated herein by reference in their entirety.

SEQUENCE LISTING

The Sequence Listing for this application is labeled "113828.000024_Sequence Listing.txt", which was created on May 6, 2020 and is 4 Kilobytes. The entire content is incorporated herein by reference in its entirety.

The present invention relates to a method, in particular an in vitro method, for identifying specific immune cells, in particular MDSCs, comprising analyzing a modification, preferably the methylation status, of at least one CpG position in the mammalian gene region for endoplasmatic reticulum-golgi intermediate compartment 1 (ERGIC1), wherein a demethylation or lack of methylation or modification of said gene region is indicative for an MDSC, when compared to a non-MDSC. The analyses according to the invention can identify specific sub-populations of MDSCs, namely monocytic MDSCs (mMDSCs) on an epigenetic level and distinguish them from all other cells in complex samples, such as, for example, other blood or immune cells. The present invention furthermore provides an improved method for quantifying mMDSCs, in particular in complex samples. The method can be performed without a step of purifying and/or enriching cells, preferably in whole blood and/or non-trypsinized tissue.

Furthermore, the present invention relates to a kit for performing the above methods as well as respective uses thereof. It is one aim of this invention to provide a novel, more robust means to quantitatively detect and measure MDSCs of the blood within any solid organs or tissue or any other body fluid of a mammal.

BACKGROUND OF THE INVENTION

MDSC (myeloid-derived suppressor cells) are a heterogenous group of immune cells from the myeloid lineage, a family of cells that originate from bone marrow stem cells. Certain sub-populations of MDSCs namely mMDSCs, strongly expand in pathological situations such as chronic infections and cancer, as a result of an altered hematopoiesis. MDSCs are discriminated from other myeloid cell types in that they possess strong immunosuppressive activities rather than immunostimulatory properties. Similar to other myeloid cells, MDSCs interact with other immune cell types including T cells, dendritic cells, macrophages and natural killer cells to regulate their functions. Although their mechanisms of action are not clear yet, clinical and experimental evidence suggests that cancer tissues with high infiltration of MDSCs are associated with poor patient prognosis and resistance to therapies.

Even though almost all cells in an individual contain the exact same complement of DNA code, higher organisms must impose and maintain different patterns of gene expression in the various types of tissue. Most gene regulation is transitory, depending on the current state of the cell and changes in external stimuli. Persistent regulation, on the other hand, is a primary role of epigenetics-heritable regulatory patterns that do not alter the basic genetic coding of the DNA. DNA methylation is the archetypical form of epigenetic regulation; it serves as the stable memory for cells and performs a crucial role in maintaining the long-term identity of various cell types. Recently, other forms of epigenetic regulation were discovered. In addition to the "fifth base" 5-methylcytosine (mC), a sixth (5-hydroxymethylcytosine, hmC), seventh (5-formylcytosine, fC) and eighth (5-carboxycytosine, cC) can be found (Michael J. Booth et al. Quantitative Sequencing of 5-Methylcytosine and 5-Hydroxymethylcytosine at Single-Base Resolution Science 18 May 2012, Vol. 336 no. 6083 pp. 934-937).

The primary target of mentioned DNA modifications is the two-nucleotide sequence Cytosine-Guanine (a 'CpG site'); within this context cytosine (C) can undergo a simple chemical modification to become formylated, methylated, hydroxymethylated, or carboxylated. In the human genome, the CG sequence is much rarer than expected, except in certain relatively dense clusters called 'CpG islands'. CpG islands are frequently associated with gene promoters, and it has been estimated that more than half of the human genes have CpG islands (Antequera and Bird, Proc Natl Acad Sci USA 90: 11995-9, 1993).

Aberrant methylation of DNA is frequently associated with the transformation from healthy to cancerous cells. Among the observed effects are genome-wide hypomethylation, increased methylation of tumor suppressor genes, and hypomethylation of many oncogenes (reviewed, for example, by Jones and Laird, Nature Genetics 21:163-167, 1999; Esteller, Oncogene 21:5427-5440, 2002; and Laird, Nature Reviews/Cancer 3:253-266, 2003). Methylation profiles have been recognized to be tumor specific (i.e., changes in the methylation pattern of particular genes or even individual CpGs are diagnostic of particular tumor types), and there is now an extensive collection of diagnostic markers for bladder, breast, colon, esophagus, stomach, liver, lung, and prostate cancers (summarized, for example, by Laird, Nature Reviews/Cancer 3:253-266, 2003).

For one of the recently described modification of cytosine, 5-hydroxymethylation, the utility of oxidative bisulfite sequencing to map and quantify 5hmC at CpG islands was shown (Michael J. Booth et al. Quantitative Sequencing of 5-Methylcytosine and 5-Hydroxymethylcytosine at Single-Base Resolution Science 18 May 2012, Vol. 336 no. 6083 pp. 934-937). High levels of 5hmC were found in CpG islands associated with transcriptional regulators and in long interspersed nuclear elements. It is suggested that these regions might undergo epigenetic reprogramming in embryonic stem cells.

Kirby et al. (Genome-wide DNA methylation measurements in prostate tissues uncovers novel prostate cancer diagnostic biomarkers and transcription factor binding patterns. BMC Cancer 2017 (1): 273, pp 1-10) describes a region close to ERGIC1 as a diagnostic marker for prostate cancer.

Zhang et al. (Epigenetics in myeloid derived suppressor cells: a sheathed sword towards cancer. Oncotarget (2016) 7 (35): 57452-57463) summarizes data relating to epigenetic regulation in MDSCs.

US 2016-0237493 describes a method and apparatus for identifying biomarkers and in particular for identifying biomarkers for use in making clinical assessments, such as early diagnostic, diagnostic, disease stage, disease severity, disease subtype, response to therapy or prognostic assessments. In one particular example, the techniques are applied to allow assessments of patients suffering from, suspected of suffering from, or with clinical signs of SIRS (Systemic Inflammatory Response Syndrome) being either infection-negative SIRS or infection-positive SIRS. EPIC1 is mentioned as an IRS biomarker gene.

WO 2012/162660 describes methods using DNA methylation arrays are provided for identifying a cell or mixture of cells and for quantification of alterations in distribution of cells in blood or in tissues, and for diagnosing, prognosing and treating disease conditions, particularly cancer. The methods use fresh and archival samples.

In view of the above, it is an object of the present invention to provide an improved and in particular robust method based on DNA-methylation analysis as a superior tool in order to more conveniently and reliably detect, identify, discriminate, and quantify specific immune cells, in particular certain subgroups of MDSCs.

The present invention solves the above object by providing a method for identifying certain myeloid-derived suppressor cells (MDSCs) in a sample derived from a mammal, comprising analyzing a modification, preferably the methylation status, of at least one CpG position in the mammalian gene region for endoplasmatic reticulum-golgi intermediate compartment 1 (ERGIC1), wherein preferably said gene region as analyzed is a sequence according to SEQ ID NO: 1, and wherein a demethylation or lack of methylation or modification of said gene region is indicative for monocytic MDSCs, when compared to a non-MDSC. The present method is able to identify monocytic myeloid-derived suppressor cells (mMDSC) which are an important component of the immunosuppressive milieu. In mice, monocytic MDSCs express high levels of the Ly6C surface marker with low or no expression of the Ly6G marker, while another group called granulocytic MDSCs express Ly6C and high levels of Ly6G. For the purpose of the present invention, human mMDSCs are defined as CD15−CD14+ CD33+ CD11b+ HLADR+. Granulocytic human MDSCs are CD15+. A third fraction seems to be CD15+ CD14+, and thus the present invention detects non-CD15 MDSCs.

The gene for human ERGIC1 is found on Ensembl. Ensembl-ID: ENSG00000113719.

In the context of the present invention, the gene region shall comprise all of the genomic regions relating to and encoding for ERGIC1. Thus, included are enhancer regions, promoter region(s), introns, exons, and non-coding regions (5'- and/or 3'-regions) that belong to ERGIC1. Preferred is thus a method according to the present invention, wherein the at least one CpG position is present in the 5' region upstream from the transcription start, promoter region, the 5' or 3' untranslated regions, exon, intron, exon/intron border and/or in the 3' region downstream of the transcriptional stop of the gene as analyzed. Preferably, said mammal is a mouse, goat, dog, pig, cat, cow rat, monkey or human. The samples can be suitably pooled, if required.

The present invention is further based on the surprising identification of a region of the ERGIC1 gene by the inventors, as specific epigenetic marker, allowing the identification of MDSCs as well as the clinical routine application of said analysis.

In the context of the present invention, the genomic region of ERGIC1, in particular according to SEQ ID NO: 1 allows the identification of mMDSCs. Surprisingly, the discriminatory pattern of bisulfite convertible and non-convertible cytosine is particularly and even exclusively limited to the genomic region according to SEQ ID NO: 1 of mMDSCs as shown using the amplicon according to SEQ ID NO: 1, and in particular in the bisulfite converted sequences according to SEQ ID NO: 2 or 3.

The inventors could demonstrate that in mMDSCs the CpG motifs as disclosed are almost completely demethylated (i.e. to more than 70%, preferably 80%, preferably, more than 90% and most preferred more than 95%), whereas the same motifs are completely methylated in all other immune cells.

The differential methylation of the CpG motifs within the aforementioned regions is a valuable tool to identify mMDSCs, such as will be required/or at least of some value for identifying and quantifying said cells in autoimmune diseases, transplant rejections, cancer, allergy, primary and secondary immunodeficiencies, such as, for example, HIV infections and AIDS, Graft versus Host (GvH), hematologic malignancies, rheumatoid arthritis, multiple sclerosis, or a cytotoxic T cell related immune status in any envisionable diagnostic context. The assay allows measurement of mMDSCs without purification or any staining procedures.

Another preferred aspect of the method according to the present invention then further comprises a quantification of the relative amount of mMDSCs based on comparing relative amounts of said methylation frequency in the region as analyzed with relative amounts of the methylation frequency in a control gene, such as, for example, GAPDH. Said quantification is thus achieved based on the ratio of the bisulfite convertible DNA to non-convertible DNA in the genetic region of ERGIC1 (e.g. of SEQ ID NO: 1) as described and analyzed herein. Most preferred is a quantification of the relative amount of mMDSCs is based on an (preferably parallel or simultaneous) analysis of the relative amount of bisulfite convertible DNA of cell-specific region for ERGIC1, and of the relative amount of bisulfite convertible DNA of cell-unspecific genes (preferably designated "control genes" or "control regions", such as, for example, the gene for GAPDH).

In a further preferred embodiment of the method according to the present invention, said analysis of bisulfite convertibility comprises amplification with at least one primer of suitable primer pairs that can be suitably designed based on SEQ ID NO: 1, preferably oligomers according to any of SEQ ID NOs: 4 to 11.

In contrast to FACS and mRNA measurements, using the methods according to the present invention, the measurement(s) and analyses can be done independent of purification, storage—and to quite some extent—also of tissue quality.

Preferably, the amplification involves a polymerase enzyme, a PCR or chemical amplification reaction, or other amplification methods as known to the person of skill as described below, e.g. in the context of MSP, HeavyMethyl, Scorpion, MS-SNUPE, MethylLight, bisulfite sequencing, methyl specific restriction assays and/or digital PCR (see, for example Kristensen and Hansen PCR-Based Methods for Detecting Single-Locus DNA Methylation Biomarkers in Cancer Diagnostics, Prognostics, and Response to Treatment Clinical Chemistry 55:8 1471-1483 (2009)).

With the amplification, an amplicon of the ERGIC1 gene region is produced that is a particularly preferred "tool" for performing the method(s) according to the present invention. Consequently, oligomers according to any of SEQ ID NOs: 4 to 11, or an amplicon as amplified by a primer pair based on SEQ ID NOs: 4 and 5, 6 and 7, or 9 and 10 as mentioned herein constitute preferred embodiments of the present invention. Thus, the sequences of SEQ ID NOs: 1 to 3 (and, if needed, the complementary sequences thereto) can be used to design primers for amplifications, i.e. serve as "beacons" in the sequence as relevant. Similarly, additional primers and probes can be designed based on the amplicon according to SEQ ID NO: 1. Amplification can take place either in the genomic and/or bisulfite (i.e. "converted") DNA sequence.

The person of skill will furthermore be able to select specific subsets of CpG positions in order to minimize the amount of sites to be analyzed, for example at least one of CpG position selected from a CpG position in an amplicon according to SEQ ID NO: 1, and is preferably selected from CpG positions 1, 2, 3, 4, 5, 6, 7, 8, 9, 10, 11, 12, 13, 14, and 15 in the amplicon No. 2505 according to SEQ ID NO: 1. The positions are numerically counted from the 5'-end of an amplicon as generated and analyzed, and are designated in FIG. 1 as AMP2505:37, 56, 62, 71, 121, 170, 227, 234, 247, 264, 271, 389, and 421. Preferred are combinations of 3, 4, 5, 6, 7, 8, 9, or 10 positions, the analysis of which produces sufficient data and/or information in order to be informative in the context of the present invention.

The person of skill will furthermore be able to select specific subsets of CpG positions in order to minimize the amount of sites to be analyzed, for example at least one of CpG position 62 in the amplicon No. 2505 of the ERGIC1 specific bisulfite convertible region (SEQ ID NO: 1), or all sites as present on the bisulfite convertible region according to SEQ ID NO: 1. One or more of positions 234, and/or 37 may be excluded.

In order to analyze the bisulfite convertibility of CpG positions, any known method to analyze DNA methylation can be used. In a preferred embodiment of the method according to the present invention, the analysis of the methylation status comprises a method selected from methylation specific enzymatic digests, bisulphite sequencing, analysis selected from promoter methylation, CpG island methylation, MSP, HeavyMethyl, MethyLight, Ms-SNuPE or other methods relying on a detection of amplified DNA. These methods are well known to the person of skill, and can be found in the respective literature.

In a preferred embodiment of the method according to the present invention, said method is suitable for routine application, for example on a DNA-chip. Based on the above information and the respective literature, the person of skill will be able to adjust the method as above to such settings.

In yet another preferred embodiment of the methods according to the present invention, said method is performed without a step of purifying and/or enriching said cells to be identified, preferably using whole blood and/or non-trypsinized tissue.

In another preferred embodiment of the method according to the present invention, the identification comprises a distinction of said MDSCs from all major peripheral blood cell types and/or non-blood cells, preferably, but not limited to, from CD19+ B cells; CD8+ cytotoxic T cells; CD15+ granulocytes; various MDSC fractions, including CD14+ only, CD14+ CD124+, CD14+ HLADR−, and CD14CD15 double positive cells; CD56+NK cells; and CD4+ T helper cells.

In yet another preferred embodiment of the method according to the present invention, the sample is selected from a mammalian body fluid, including mammalian blood samples, or a tissue, organ or a sample of leukocytes or a purified or separated fraction of such tissue, organ or leukocytes or a cell type sample. The samples can be suitably pooled, if required.

Another preferred aspect of the method according to the present invention then further comprises the step of concluding on the immune status of said mammal based on said MDSCs. MDSCs can be quantified and be used as a benchmark to relatively quantify further detailed subpopulations, or it can be used as a predictive and/or screening and/or diagnostic and/or prognostic and/or adverse events detecting factor, or it can be used to finally detect this population to determine the overall immune activity status.

In yet another preferred embodiment of the methods according to the present invention, the mammal suffers from or is likely to suffer from autoimmune diseases, transplant rejections, infection diseases, cancer, and/or allergy as but not limited to *Trypanosoma cruzi*-infection, Malaria and HIV infection; Hematologic Malignancies as but not limited to chronic Myelogenous Leukemia, Multiple Myeloma, Non Hodgkin's Lymphoma, Hodgkin's Disease, chronic Lymphocytic Leukemia, Graft versus Host and Host versus Graft Disease, Mycosis fungoides, Extranodal T cell lymphoma, Cutaneous T cell lymphomas, Anaplastic large cell lymphoma, Angioimmunoblastic T cell lymphoma and other T-cell, B-cell and NK cell neoplasms, T cell deficiencies such as but not limited to lymphocytopenia, severe combined immunodeficiency (SCID), Omenn syndrome, Cartilage-hair hypoplasia, acquired immune deficiency syndrome (AIDS), and hereditary conditions such as DiGeorge syndrome (DGS), chromosomal breakage syndromes (CBSs), multiple sclerosis, rheumatoid arthritis, systemic lupus erythematosus, Sjögren's syndrome, systemic sclerosis, dermatomyositis, primary biliary cirrhosis, primary sclerosing cholangitis, ulcerative colitis, Crohn's disease, psoriasis, vitiligo, bullous pemphigoid, alopecia areata, idiopathic dilated cardiomyopathy, type 1 diabetes mellitus, Graves' disease, Hashimoto's thyroiditis, myasthenia gravis, IgA nephropathy, membranous nephropathy, and pernicious anemia; and B-cell and T-cell combined disorders such as but not limited to ataxia telangiectasia (AT) and Wiskott-Aldrich syndrome (WAS); and carcinomas such as but not limited to breast cancer, colorectal cancer, gastric cancer, pancreatic cancer, hepatocellular carcinoma, cholangiocarcinoma, melanoma, and head and neck cancer.

Another preferred aspect of the method according to the present invention then relates to a method as above, further comprising measuring and/or monitoring the amount of mMDSCs in response to chemical and/or biological substances that are provided to said mammal, i.e. in response to a treatment of said patient. Said method comprises the steps as above, and comparing said relative amount of said cells as identified to a sample taken earlier or in parallel from the same mammal, and/or to a control sample. Based on the results as provided by the method(s) of the invention, the attending physician will be able to conclude on the immune status of the patient, and adjust a treatment of the underlying disease accordingly.

Preferably, said method is performed without a step of purifying and/or enriching cells, preferably in whole blood and/or non-trypsinized tissue, or any other biological sample potentially containing said mMDSCs as e.g. a sample for cell transfer into a patient.

Another preferred aspect of the method according to the present invention then relates to a method as above, further comprising formulating said mMDSCs as identified for transplantation into a patient. Pharmaceutical preparations for these purposes and methods for their production are performed according to methods known in the art of transplantation medicine.

Another preferred aspect of the method according to the present invention relates to an oligomer according to any of SEQ ID NOs: 4 to 11, or an amplicon according to SEQ ID NOs: 1 to 3.

Yet another preferred aspect of the present invention then relates to a kit for identifying, quantifying, and/or monitoring MDSCs in a mammal based on the analysis of the bisulfite accessibility of CpG positions in the gene region of ERGIC1, comprising components for performing a method according to any of claims 1 to 12, in particular a kit comprising a) a bisulfite reagent, and b) materials for the analysis of the methylation status of CpG positions selected from the CpG positions in the region according to SEQ ID NO: 1, such as an oligomer selected from the sequences according to SEQ ID NOs: 4 to 11.

The present invention also encompasses the use of oligomers or amplicon or a kit according to the present invention for identifying and/or for monitoring MDSCs in a mammal as described herein.

As mentioned above, recently three new cytosine modifications were discovered. Therefore, it is expected that future scientific findings will correct epigenetic patterns of modification described in the past. These past patterns of cytosine modification encompass bisulfite convertible (non-methylated, non-modified) and non-convertible (methylated, modified) cytosine. Both termini need to be corrected, as described. According to the novel scientific findings (i) non-bisulfite convertible cytosine encompasses 5-methylcytosine (mC) and 5-hydroxymethylcytosine (hmC), and (ii) bisulfite convertible (i.e. the "bisulfite convertibility") cytosine encompasses 5-formylcytosine (fC), 5-carboxycytosine (cC), as well as non-modified cytosine.

Additionally, past inventions are based on (i) the ratio of bisulfite convertible cytosine to whole amount of chromatin (cell-type independent, 100% bisulfite convertible DNA locus) or (ii) on the ratio of bisulfite convertible cytosine (fC, cC, non-modified cytosine) to non-bisulfite convertible cytosine (hmC and mC). These ratios characterize cell type, cell differentiation, cell stage as well as pathological cell stages. Therefore, new techniques will result in novel, more specific ratios and might supplement current cell specific, cell state specific as well as pathological patterns of epigenetic modifications and therefore, define potential novel biomarkers. Novel ratios to be discovered as biomarkers can be defined as:

Biomarker Ratio=$a/b$ $a=\Sigma$ (C and/or mC and/or hmC and/or fC and/or cC)
$b=\Sigma$ (C and/or mC and/or hmC and/or fC and/or cC),
whereby a and b differs from each other by one to four kinds of modifications. Discovery of novel DNA modifications will enlarge this enumeration.

For the purpose of definition for the present application, "epigenetic modifications" in the DNA sequence is referred to by the terminology of (i) bisulfite convertible cytosine (5-formylcytosine, (fC) and/or 5-carboxycytosine (cC)) and (ii) non-bisulfite convertible cytosine ((including 5-methylcytosine (mC), 5-hydroxymethylcytosine, (hmC)). As both kinds of methylation, mC and hmC, are not bisulfite convertible, it is not possible to distinguish between these two. Likewise, fC, cC as well as non-modified cytosine are bisulfite convertible and can also not be distinguished from each other as well. The term "methylated" DNA encompasses mC as well as hmC. The term "non-methylated" DNA encompasses fC, cC, and non-modified DNA. It is expected that novel variants of DNA modifications will be discovered in future. Each type of modification will be either bisulfite convertible or not. However, since the present method reliably distinguishes between the two groups, these novel modifications will also be usable as markers.

Furthermore, apart from the modifications of DNA, also histones undergo posttranslational modifications that alter their interaction with DNA and nuclear proteins. Modifications include methylation, acetylation, phosphorylation, ubiquitination, sumoylation, citrullination, and ADP-ribosylation. The core of the histones H2A, H2B, and H3 can also be modified. Histone modifications act in diverse biological processes such as gene regulation, DNA repair, chromosome condensation (mitosis) and spermatogenesis (meiosis). Also for these modifications a specific pattern of modification is specific for different cell types, cell stages, differentiation status and such a pattern can be analyzed for bisulfite convertibility or similar methods in order to identify certain cells and cell stages. The present invention also encompasses a use of these modifications.

In summary, using the ERGIC1 genetic region and in particular the amplicon as described herein as a marker, the inventors very specifically identified, quantified and particularly differentiated MDSCs, and in their relation to other cell types in a sample, for example to other blood cells.

The invention will now be further described based on the following examples and with reference to the accompanying figures and the sequence listing, without being limited thereto. For the purposes of the present invention, all references as cited herein are incorporated by reference in their entireties.

SEQ ID NO: 1 represents the genomic sequence of amplicon AMP2505 according to the present invention.

SEQ ID NO: 2 represents the bisulfite converted (b2F), previously modified (CpG) sequence with conversion resistant CpG residues.

SEQ ID NO: 3 represents the bisulfite converted (b2F), previously unmodified (TpG) sequence with no conversion resistant CpG residues.

SEQ ID NO: 4 to 11 show oligomers (primers and probes) as used in the present invention.

EXAMPLES

Example 1

In order to identify the target mMDSC subpopulation, qPCR was performed on bisulphite converted samples stemming from the human genomic region according to sequence AMP2505, SEQ ID NO: 1. Relevant CpGs are indicated bold and underlined.

GAGGGAATGAGTAGGTGAACAAACGAGTGAGTTTTTCGCCTCACTCCCTG

GCACTCGGCACCGAGGGCTCCGACAGGCTGGTGGCCAGGGCTGACCAGCC

AGAGTTTCATCTAAAAGCCTCGATGGCTATTTTTGGGACAAATGACCCAC

CACTTCCAATGACTTGCTCCGAAATGGCATCTAATTTCATTAAGCCTTGG

AAACAGTGACATCACAAGTGCCTGCCCGGTAGCCGCCCACATATGGCGAA

CCACAGAGTGATCCGAGATTCGTCTGCAAGAACAGGGGAGAACTAAGGTC

CCAAGCAGCAAAAGTTAAAATAGCAAAGCTGAGGCATTCTGCTATGAAAA

GAAATTACAGATGAAATCCATTAGTCAGACATTTCCAGCGGCAGTTTCCT

TGCTTGGGAGCAGGGGAAGACGTGTTTATTCGGGGTTGGGCTCTGCAGCC

ATTCC

SEQ ID NO: 2 represents the bisulfite converted (b2F), previously modified (CpG) sequence with conversion resistant CpG residues. Relevant CpGs are indicated bold and underlined.

AAAAAAATAAATAAATAAACAAACGAATAAATTTTTCGCCTCACTCCCTA

ACACTCGACACCGAAAACTCCGACAAACTAATAACCAAAACTAACCAACC

AAAATTTCATCTAAAAACCTCGATAACTATTTTTAAAACAAATAACCCAC

CACTTCCAATAACTTACTCCGAAATAACATCTAATTTCATTAAACCTTAA

AAACAATAACATCACAAATACCTACCCGATAACCGCCCACATATAACGAA

CCACAAAATAATCCGAAATTCGTCTACAAAAACAAAAAAAACTAAAATC

CCAAACAACAAAAATTAAAATAACAAAACTAAAACATTCTACTATAAAAA

AAAATTACAAATAAATCCATTAATCAAACATTTCCAACGACAATTTCCT

TACTTAAAAACAAAAAAAAACGTATTTATTCGAAATTAAACTCTACAACC

ATTCC

SEQ ID NO: 3 represents the bisulfite converted (b2F), previously unmodified (TpG) sequence with no conversion resistant CpG residues. Relevant positions are indicated bold and underlined.

AAAAAAATAAATAAATAAACAAACAATAAATTTTTCACCTCACTCCCTA

ACACTCAACACCAAAAACTCCAACAAACTAATAACCAAAACTAACCAACC

AAAATTTCATCTAAAAACCTCAATAACTATTTTTAAAACAAATAACCCAC

CACTTCCAATAACTTACTCCAAAATAACATCTAATTTCATTAAACCTTAA

AAACAATAACATCACAAATACCTACCCATAACCACCCACATATAACAAA

CCACAAAATAATCCAAAATTCATCTACAAAAACAAAAAAAACTAAAATC

CCAAACAACAAAAATTAAAATAACAAAACTAAAACATTCTACTATAAAAA

AAAATTACAAATAAATCCATTAATCAAACATTTCCAACAACAATTTCCT

TACTTAAAAACAAAAAAAAACATATTTATTCAAAATTAAACTCTACAACC

ATTCC

Figure 1:
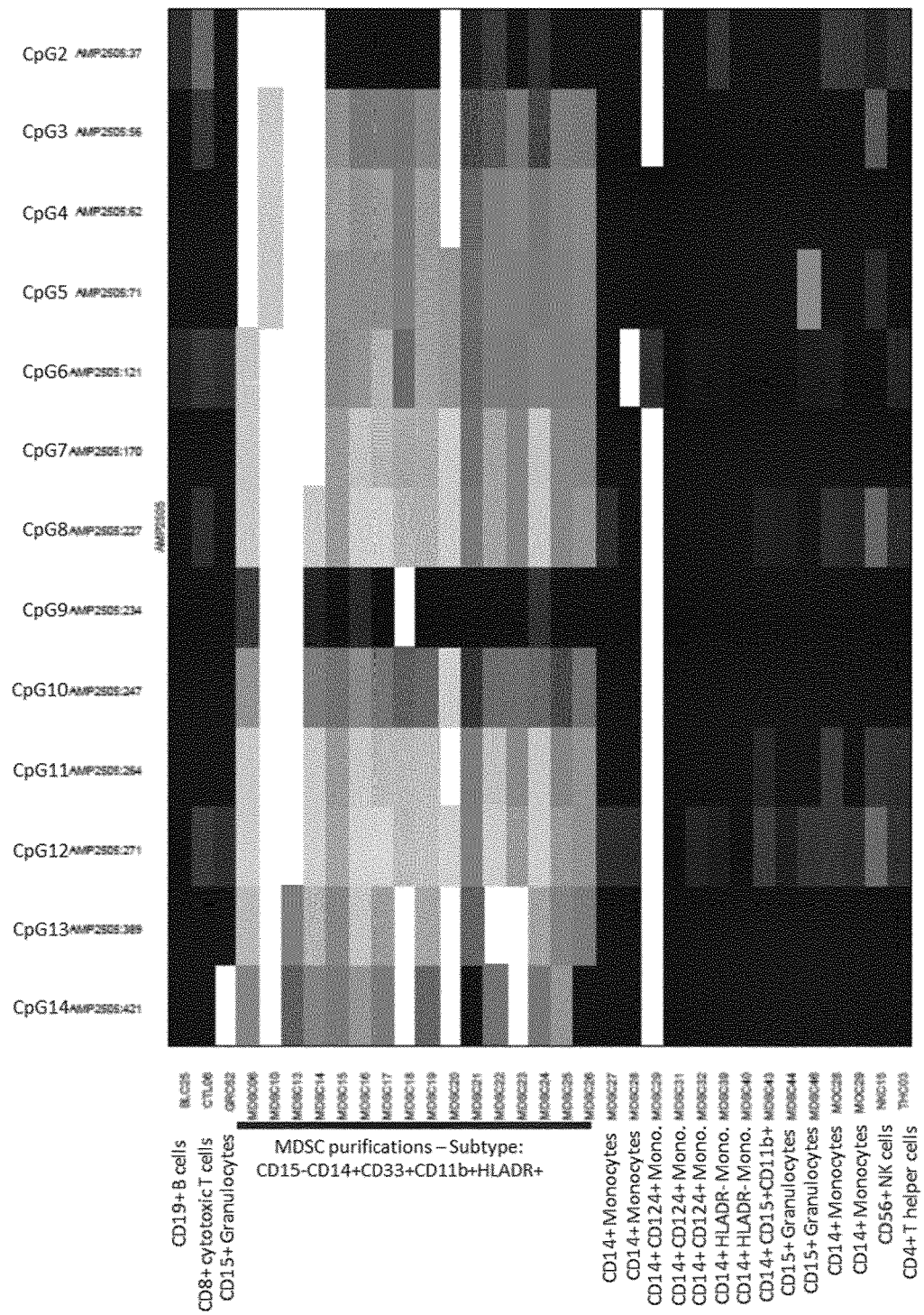
FIG. 1 shows the analysis of CpG sites on amplicon No. 2505 (SEQ ID NO: 1) according to the invention. The horizontal boxes in the table correspond to the CpG positions in the amplicon as analyzed (e.g. CpG 2, 3, 4, . . . etc.) with the positions indicated (37, 56, 62, 71, 121, 170, 227, 234, 247, 264, 271, 389, and 421 corresponding to CpG 2, 3, . . . etc.), and the columns correspond to the cell types as analyzed. Positions 1 (24), and 15 (431) as also analyzed are not shown. The vertical boxes (columns) correspond to the cellular fractions as analyzed.

For the actual epigenetic profiling of the amplicon region in blood cell subtypes, the immune cell populations as analyzed were as follows (see FIG. 1)

1. As target population: CD15− CD14+ CD33+ CD11b+, HLADR+
2. CD19+ B cells; CD8+ cytotoxic T cells; CD15+ granulocytes; various MDSC fractions, including CD14+ only, CD14+CD124+, CD14+HLADR−, CD14CD15 double positive; CD56+NK cells; and CD4+ T helper cells.

The following primers and probe were used for the qPCR (TpG variant; demethyl-specific; CpG variant; methyl-specific):

| | | |
|---|---|---|
| Forward amplification primer | 2505-fwd | GAGGGAATGAGTAGGTGAATAA (SEQ ID NO: 4) |
| Reverse amplification primer | 2505-rev | AAAATAACTACAAAACCCAACC (SEQ ID NO: 5) |
| Forward primer TpG-specific | 2505_TpG-fwd | CCCTAACACTCAACACCA (SEQ ID NO: 6) |
| Reverse primer TpG-specific | 2505_TpG-rev | GGGTTATTTGTTTTAAAAATAGTTATTG (SEQ ID NO: 7) |
| Probe TpG-specific | 2505_TpG-pro | TGGTTATTAGTTTGTTGGAGTTTTTGGT (SEQ ID NO: 8) |
| Forward primer CpG-specific | 2505_CpG-fwd | CCCTAACACTCGACACCG (SEQ ID NO: 9) |
| Reverse primer CpG-specific | 2505_CpG-rev | GGGTTATTTGTTTTAAAAATAGTTATC (SEQ ID NO: 10) |
| Probe CpG-specific | 2505_CpG-pro | TTTTGGTTATTAGTTTGTCGGAGTTTTCGG (SEQ ID NO: 11) |

Figure 2:
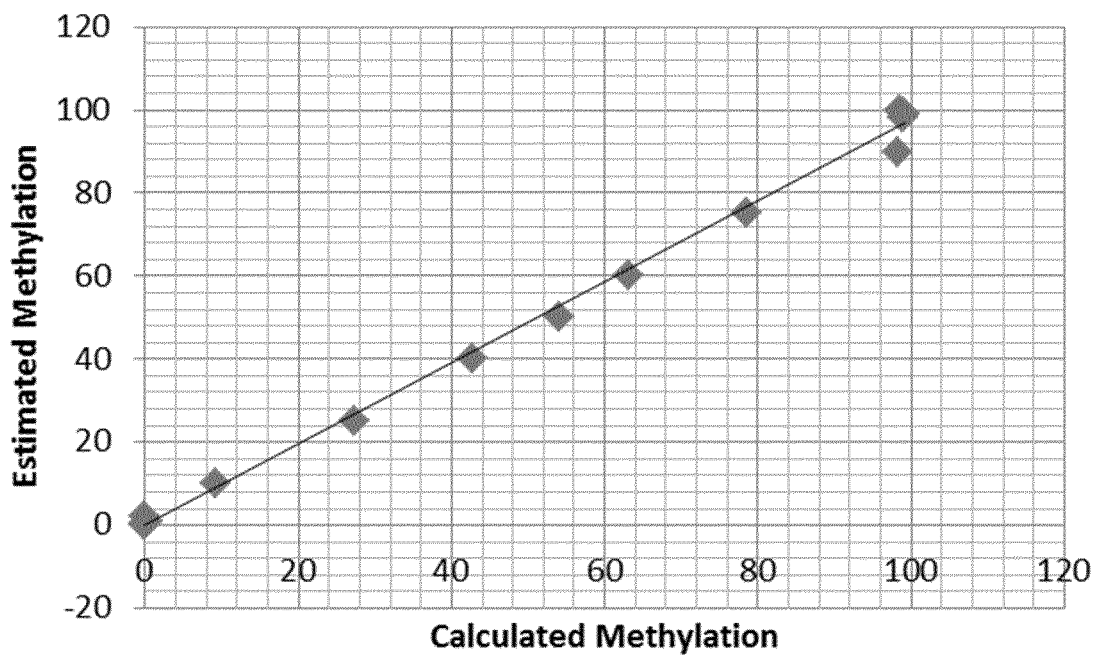
FIG. 2 shows data regarding the linearity and specificity of the TpG-specific PCR-system according to the present invention.

The linearity and specificity of the TpG-specific PCR-system was demonstrated using test-templates (plasmid-DNA) containing either CpG or TpG variants of the in silico converted sequence. The corresponding values between the actually measured qPCR results (calculated methylation) compared to the prepared dilutions (estimated methylation) are shown in FIG. 2. The cell type specificity (as measured by qPCR) was found to be as follows:

| Type of immune cell | qPCR-Detection [%] |
|---|---|
| Target subpopulation of MDSCs | 68.5 |
| CD8+ T-cells | 0.9 |
| CD56+ NK-cells | 0.1 |
| B-cells | 0.1 |
| CD14+ monocytes | 0.1 |
| CD4+ T-cells | 0.5 |

The invention claimed is:

1. A method for producing an amplicon, the method comprising
  a) bisulfite treating isolated genomic DNA from a human cell sample comprising cluster of differentiation (CD) 15−CD14+ CD33+ CD11b+ human leukocyte antigen DR (HLADR)+ monocytic myeloid-derived suppressor cells (mMDSCs) to generate bisulfite treated DNA, and
  b) amplifying from the bisulfite treated DNA a region of endoplasmic reticulum-golgi intermediate compartment 1 (ERGIC 1) gene comprising SEQ ID NO: 1 to thereby generate the amplicon, wherein the amplicon comprises a cytosine-adenine (CA) at at least CpG positions at nucleotides 56, 62, and 71 relative to SEQ ID NO: 1.

2. The method according to claim 1, wherein said CpG positions are present in the intron of said gene region.

3. The method according to claim 1, wherein the amplicon further comprises at least one CA at a CpG position selected from nucleotide positions 121, 170, 227, and 247 relative to SEQ ID NO: 1.

4. The method according to claim 1, further comprising detecting the CA by a method selected from a methylation specific enzymatic digest, bisulfite sequencing, promoter methylation analysis, CpG island methylation analysis, methylation specific polymerase chain reaction (MSP), HeavyMethyl, MethyLight, methylation-sensitive single-nucleotide primer extension (Ms-SNuPE), and other methods relying on a detection of amplified DNA.

5. The method according to claim 1, wherein said sample is selected from a body fluid, a blood sample, a tissue, an organ, bone marrow, a cell type blood sample, or a sample of blood lymphocytes.

6. The method according to claim 1, wherein said method is performed without a step of purifying and/or enriching said cell sample.

7. The method according to claim 1, wherein said cell sample is from a mammal that suffers from or is likely to suffer from autoimmune diseases, transplant rejections, infection diseases, cancer and/or allergy.

8. The method of claim 1, wherein the method is performed using a kit comprising:
  a) a bisulfite reagent, and
  b) materials for detecting the at least one CA.

9. The method of claim 1, wherein the amplifying is performed with a polymerase chain reaction (PCR) using an oligomer comprising the sequence of any one of SEQ ID NOs: 4 to 11.

10. The method according to claim 1, wherein the amplicon further comprises CA at at least two CpG positions selected from nucleotide positions 121, 170, and 227 relative to SEQ ID NO: 1.

11. The method according to claim 1, wherein the human cell sample is whole blood and/or non-trypsinized tissue.

12. The method of claim 1, wherein the amplicon further comprises at least three CA at CpG positions selected from nucleotide positions 121, 170, 227, and 247 relative to SEQ ID NO: 1.

13. The method of claim 1, wherein the amplicon comprises CA at CpG positions 56, 62, 71, and 121 relative to SEQ ID NO: 1.

14. A method of producing an amplicon, the method comprising:
  a) bisulfite treating isolated genomic DNA from a human cell sample comprising cluster of differentiation (CD) 15−CD14+CD33+CD11b+ human leukocyte antigen DR (HLADR)+ monocytic myeloid-derived suppressor cells (mMDSCs) to generate bisulfite treated DNA where unmethylated cytosines are converted to uracils, and
  b) amplifying with polymerase chain reaction (PCR) a region of the bisulfite treated DNA to produce an amplicon comprising nucleotides 46-148 of SEQ ID NO: 3 and having cytosine-adenine (CA) at nucleotide positions 56, 62, and 71 relative to SEQ ID NO: 3.

15. A method of producing an amplicon, the method comprising:
  a) bisulfite treating isolated genomic DNA from a human cell sample comprising cluster of differentiation (CD) 15−CD14+CD33+CD11b+ human leukocyte antigen DR (HLADR)+ monocytic myeloid-derived suppressor cells (mMDSCs) to generate bisulfite treated DNA where unmethylated cytosines are converted to uracils, and
  b) amplifying with polymerase chain reaction (PCR) a region of the bisulfite treated DNA to produce an amplicon comprising nucleotides 46-148 of SEQ ID NO: 3 and having cytosine-adenine (CA) at nucleotide positions 62 and 71 relative to SEQ ID NO: 3.

16. The method of claim 15, wherein the amplicon further comprises cytosine-adenine (CA) at nucleotide positions 56 and 121 relative to SEQ ID NO: 3.

* * * * *

SEQUENCE LISTING

<160> NUMBER OF SEQ ID NOS: 11

<210> SEQ ID NO 1
<211> LENGTH: 455
<212> TYPE: DNA
<213> ORGANISM: Homo sapiens

<400> SEQUENCE: 1
gagggaatga gtaggtgaac aaacgagtga gttttcgcc tcactccctg gcactcggca    60
ccgagggctc cgacaggctg gtggccaggg ctgaccagcc agagtttcat ctaaaagcct   120
cgatggctat ttttgggaca aatgacccac cacttccaat gacttgctcc gaaatggcat   180
ctaatttcat taagccttgg aaacagtgac atcacaagtg cctgccggt agccgcccac   240 atatggcgaa ccacagagtg atccgagatt cgtctgcaag aacaggggag aactaaggtc   300
ccaagcagca aaagttaaaa tagcaaagct gaggcattct gctatgaaaa gaaattacag   360
atgaaatcca ttagtcagac atttccagcg gcagtttcct tgcttgggag caggggaaga   420
cgtgtttatt cggggttggg ctctgcagcc attcc                              455

<210> SEQ ID NO 2
<211> LENGTH: 455
<212> TYPE: DNA
<213> ORGANISM: Homo sapiens

<400> SEQUENCE: 2
aaaaaaataa ataaataaac aaacgaataa atttttcgcc tcactcccta acactcgaca    60
ccgaaaactc cgacaaacta ataaccaaaa ctaaccaacc aaaatttcat ctaaaaacct   120
cgataactat ttttaaaaca aataacccac cacttccaat aacttactcc gaaataacat   180
ctaatttcat taaaccttaa aaacaataac atcacaaata cctacccgat aaccgcccac   240
atataacgaa ccacaaaata atccgaaatt cgtctacaaa aacaaaaaaa aactaaaatc   300
ccaaacaaca aaaattaaaa taacaaaact aaaacattct actataaaaa aaaattacaa   360
ataaaatcca ttaatcaaac atttccaacg acaatttcct tacttaaaaa caaaaaaaaa   420
cgtatttatt cgaaattaaa ctctacaacc attcc                              455

<210> SEQ ID NO 3
<211> LENGTH: 455
<212> TYPE: DNA
<213> ORGANISM: Homo sapiens

<400> SEQUENCE: 3
aaaaaaataa ataaataaac aaacaaataa attttcacc tcactcccta acactcaaca    60
ccaaaaactc caacaaacta ataaccaaaa ctaaccaacc aaaatttcat ctaaaaacct   120

```
caataactat ttttaaaaca aataacccac cacttccaat aacttactcc aaaataacat    180
ctaatttcat taaaccttaa aaacaataac atcacaaata cctaccccat aaccacccac    240
atataacaaa ccacaaaata atccaaaatt catctacaaa aacaaaaaaa aactaaaatc    300
ccaaacaaca aaaattaaaa taacaaaact aaaacattct actataaaaa aaaattacaa    360
ataaaatcca ttaatcaaac atttccaaca acaatttcct tacttaaaaa caaaaaaaaa    420
catatttatt caaaattaaa ctctacaacc attcc                              455

<210> SEQ ID NO 4
<211> LENGTH: 22
<212> TYPE: DNA
<213> ORGANISM: Homo sapiens

<400> SEQUENCE: 4
gagggaatga gtaggtgaat aa                                             22

<210> SEQ ID NO 5
<211> LENGTH: 22
<212> TYPE: DNA
<213> ORGANISM: Homo sapiens

<400> SEQUENCE: 5
aaaataacta caaaacccaa cc                                             22

<210> SEQ ID NO 6
<211> LENGTH: 18
<212> TYPE: DNA
<213> ORGANISM: Homo sapiens

<400> SEQUENCE: 6
ccctaacact caacacca                                                  18

<210> SEQ ID NO 7
<211> LENGTH: 28
<212> TYPE: DNA
<213> ORGANISM: Homo sapiens

<400> SEQUENCE: 7
gggttatttg ttttaaaaat agttattg                                       28

<210> SEQ ID NO 8
<211> LENGTH: 28
<212> TYPE: DNA
<213> ORGANISM: Homo sapiens

<400> SEQUENCE: 8
tggttattag tttgttggag tttttggt                                       28

<210> SEQ ID NO 9
<211> LENGTH: 18
<212> TYPE: DNA
<213> ORGANISM: Homo sapiens

<400> SEQUENCE: 9
ccctaacact cgacaccg                                                  18

<210> SEQ ID NO 10
<211> LENGTH: 27
<212> TYPE: DNA
<213> ORGANISM: Homo sapiens
```

-continued

```
<400> SEQUENCE: 10
gggttatttg ttttaaaaat agttatc                                      27

<210> SEQ ID NO 11
<211> LENGTH: 30
<212> TYPE: DNA
<213> ORGANISM: Homo sapiens

<400> SEQUENCE: 11
ttttggttat tagtttgtcg gagttttcgg                                   30
```